(12) United States Patent
Wekell et al.

(10) Patent No.: US 9,298,889 B2
(45) Date of Patent: *Mar. 29, 2016

(54) HEALTH DATA COLLECTION TOOL

(71) Applicant: Spacelabs Healthcare LLC, Snoqualmie, WA (US)

(72) Inventors: William Oren Wekell, Maple Valley, WA (US); Robert Boyer Koenig, Redmond, WA (US); Joseph Charles Basta, Duvall, WA (US)

(73) Assignee: Spacelabs Healthcare LLC, Snoqualmie, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/557,135

(22) Filed: Dec. 1, 2014

(65) Prior Publication Data

US 2015/0134364 A1    May 14, 2015

Related U.S. Application Data

(63) Continuation of application No. 13/973,862, filed on Aug. 22, 2013, now Pat. No. 8,931,702, which is a continuation of application No. 11/716,513, filed on Mar. 9, 2007, now abandoned.

(51) Int. Cl.
*G06K 19/00* (2006.01)
*G06F 19/00* (2011.01)
(Continued)

(52) U.S. Cl.
CPC ............ *G06F 19/36* (2013.01); *A61B 5/02055* (2013.01); *A61B 5/6826* (2013.01);
(Continued)

(58) Field of Classification Search
USPC .......................... 235/435, 439, 454, 462, 472
See application file for complete search history.

(56) References Cited

U.S. PATENT DOCUMENTS 2,820,651 A    1/1958  Phillips
2,912,858 A    11/1959 Fuller
(Continued)

FOREIGN PATENT DOCUMENTS

CN    1688256      10/2005
CN    101194278     6/2008
(Continued)

OTHER PUBLICATIONS

Office Action dated Apr. 24, 2015 for U.S. Appl. No. 13/651,337.
(Continued)

*Primary Examiner* — Matthew Mikels
(74) *Attorney, Agent, or Firm* — Novel IP

(57) ABSTRACT

A portable health data tool permits a health care provider to assimilate and display a plurality of health care data from a patient and to associate the data with patient identifying information all stored in a memory contained in the tool. The tool includes a code reader for reading patient information into the tool from a bar code or other coded tag. The tool is associated with a plurality of different data assimilation devices stored with the tool's housing, including but not limited to, instruments for measuring, temperature, blood pressure, two-finger or lead wire ECG data, pulse oximetry data, sound data and picture data obtained from an optional digital camera integrated within the housing. The tool further includes data receiver and/or transmitter ports, which may be wireless or cable ports, for transferring data between the health data tool and a separate computer system that stores patient records.

9 Claims, 10 Drawing Sheets

(51) Int. Cl.
*A61B 5/0205* (2006.01)
*A61B 5/00* (2006.01)
*G06Q 50/24* (2012.01)
*H02J 7/00* (2006.01)
*A61B 5/022* (2006.01)
*A61B 5/024* (2006.01)
*A61B 5/0404* (2006.01)
*A61B 5/145* (2006.01)
*A61B 7/04* (2006.01)

(52) U.S. Cl.
CPC .......... *A61B5/6838* (2013.01); *G06F 19/322* (2013.01); *G06F 19/323* (2013.01); *G06Q 50/24* (2013.01); *H02J 7/0044* (2013.01); *A61B 5/002* (2013.01); *A61B 5/022* (2013.01); *A61B 5/02438* (2013.01); *A61B 5/0404* (2013.01); *A61B 5/145* (2013.01); *A61B 7/04* (2013.01); *A61B 2560/0295* (2013.01); *A61B 2560/0406* (2013.01); *A61B 2560/0431* (2013.01); *A61B 2560/0456* (2013.01); *A61B 2560/0475* (2013.01)

(56) References Cited

U.S. PATENT DOCUMENTS

| | | | |
|---|---|---|---|
| 3,517,639 | A | 6/1970 | Whitsel |
| 3,608,545 | A | 9/1971 | Novack |
| 3,618,592 | A | 11/1971 | Stewart |
| 3,673,863 | A | 7/1972 | Spacek |
| 3,897,606 | A | 8/1975 | Schleining |
| 3,938,551 | A | 2/1976 | Henkin |
| 4,064,826 | A | 12/1977 | Pauli |
| 4,148,312 | A | 4/1979 | Bird |
| 4,167,115 | A | 9/1979 | Stoever |
| 4,513,294 | A | 4/1985 | Anderson |
| 4,557,216 | A | 12/1985 | Demyon |
| 4,625,731 | A | 12/1986 | Quedens |
| 4,630,486 | A | 12/1986 | Miles |
| 4,697,450 | A | 10/1987 | Bachman |
| 4,869,253 | A | 9/1989 | Craig |
| 4,879,997 | A | 11/1989 | Bickford |
| 4,903,222 | A | 2/1990 | Carter |
| 4,944,305 | A | 7/1990 | Takatsu |
| 4,991,576 | A | 2/1991 | Henkin |
| 5,087,906 | A | 2/1992 | Eaton |
| 5,101,851 | A | 4/1992 | Abadi |
| 5,144,898 | A | 9/1992 | Posly |
| 5,197,480 | A | 3/1993 | Gebhardt |
| 5,213,108 | A | 5/1993 | Bredesen |
| 5,222,486 | A | 6/1993 | Vaughn |
| 5,231,981 | A | 8/1993 | Schreiber |
| 5,233,975 | A | 8/1993 | Choate |
| 5,262,944 | A | 11/1993 | Weisner |
| 5,291,182 | A | 3/1994 | Wiseman |
| 5,311,908 | A | 5/1994 | Barone |
| 5,319,363 | A | 6/1994 | Welch |
| 5,322,069 | A | 6/1994 | Gallant |
| 5,331,549 | A | 7/1994 | Crawford, Jr. |
| 5,339,826 | A | 8/1994 | Schmidt |
| 5,348,008 | A | 9/1994 | Bornn |
| 5,373,746 | A | 12/1994 | Bloss |
| 5,419,332 | A | 5/1995 | Sabbah |
| 5,438,983 | A | 8/1995 | Falcone |
| 5,467,954 | A | 11/1995 | Wekell |
| 5,473,536 | A | 12/1995 | Wimmer |
| 5,482,050 | A | 1/1996 | Smokoff |
| 5,497,766 | A | 3/1996 | Foster |
| 5,502,853 | A | 4/1996 | Singleton |
| 5,515,083 | A | 5/1996 | Casebolt |
| 5,553,296 | A | 9/1996 | Forrest |
| 5,558,418 | A | 9/1996 | Lambright |
| 5,563,495 | A | 10/1996 | Tomiyori |
| 5,584,291 | A | 12/1996 | Vapola |
| 5,586,909 | A | 12/1996 | Saba |
| 5,633,457 | A | 5/1997 | Kilar |
| 5,682,526 | A | 10/1997 | Smokoff |
| 5,684,504 | A | 11/1997 | Verhulst |
| 5,687,717 | A | 11/1997 | Halpern |
| 5,692,494 | A | 12/1997 | Pernetti |
| 5,715,813 | A | 2/1998 | Guevrekian |
| 5,718,235 | A | 2/1998 | Golosarsky |
| 5,724,025 | A | 3/1998 | Tavori |
| 5,724,985 | A | 3/1998 | Snell |
| 5,749,367 | A | 5/1998 | Gamlyn |
| 5,765,842 | A | 6/1998 | Phaneuf |
| 5,779,305 | A | 7/1998 | Hocking |
| 5,787,298 | A | 7/1998 | Broedner |
| 5,800,360 | A | 9/1998 | Kisner |
| 5,819,741 | A | 10/1998 | Karlsson |
| 5,855,550 | A | 1/1999 | Lai |
| 5,868,133 | A | 2/1999 | DeVries |
| 5,904,328 | A | 5/1999 | Leveridge |
| 5,956,013 | A | 9/1999 | Raj |
| 5,975,081 | A | 11/1999 | Hood |
| 6,005,767 | A | 12/1999 | Ku |
| 6,024,089 | A | 2/2000 | Wallace |
| 6,042,548 | A | 3/2000 | Giuffre |
| 6,048,044 | A | 4/2000 | Biggel |
| 6,050,940 | A | 4/2000 | Braun |
| 6,063,028 | A | 5/2000 | Luciano |
| 6,096,025 | A | 8/2000 | Borders |
| 6,099,093 | A | 8/2000 | Spence |
| 6,131,571 | A | 10/2000 | Lampotang |
| 6,134,537 | A | 10/2000 | Pao |
| 6,146,523 | A | 11/2000 | Kenley |
| 6,155,255 | A | 12/2000 | Lambert |
| 6,269,813 | B1 | 8/2001 | Fitzgerald |
| 6,322,502 | B1 | 11/2001 | Schoenberg |
| 6,338,823 | B1 | 1/2002 | Furukawa |
| 6,339,732 | B1 | 1/2002 | Phoon |
| 6,347,310 | B1 | 2/2002 | Passera |
| 6,383,136 | B1 | 5/2002 | Jordan |
| 6,396,583 | B1 | 5/2002 | Clare |
| 6,424,860 | B1 | 7/2002 | Karlsson |
| 6,435,690 | B1 | 8/2002 | Till |
| 6,443,889 | B1 | 9/2002 | Groth |
| D467,001 | S | 12/2002 | Buczek |
| 6,488,029 | B1 | 12/2002 | Hood |
| 6,536,430 | B1 | 3/2003 | Smith |
| 6,554,238 | B1 | 4/2003 | Hibberd |
| 6,571,227 | B1 | 5/2003 | Agrafiotis |
| 6,571,792 | B1 | 6/2003 | Hendrickson |
| 6,591,694 | B2 | 7/2003 | Tsai |
| 6,600,662 | B1 | 7/2003 | Emmert |
| 6,647,341 | B1 | 11/2003 | Golub |
| 6,650,779 | B2 | 11/2003 | Vachtesvanos |
| 6,674,837 | B1 | 1/2004 | Taskar |
| 6,692,258 | B1 | 2/2004 | Kurzweil |
| 6,692,436 | B1 | 2/2004 | Bluth |
| 6,699,187 | B2 | 3/2004 | Webb |
| 6,702,754 | B2 | 3/2004 | Ogura |
| 6,715,722 | B2 | 4/2004 | Roberts |
| 6,735,648 | B2 | 5/2004 | Onishi |
| 6,771,172 | B1 | 8/2004 | Robinson |
| 6,804,656 | B1 | 10/2004 | Rosenfeld |
| 6,824,539 | B2 | 11/2004 | Novak |
| 6,829,501 | B2 | 12/2004 | Nielsen |
| 6,931,795 | B1 | 8/2005 | Baloga |
| 6,933,931 | B2 | 8/2005 | Lubarsky, Jr. |
| 6,985,762 | B2 | 1/2006 | Brashears |
| 7,006,865 | B1 | 2/2006 | Cohen |
| 7,013,833 | B2 | 3/2006 | Lemberger |
| 7,024,569 | B1 | 4/2006 | Wright |
| 7,031,857 | B2 | 4/2006 | Tarassenko |
| 7,038,588 | B2 | 5/2006 | Boone |
| 7,076,435 | B1 | 7/2006 | McKeag |
| 7,081,091 | B2 | 7/2006 | Merrett |
| RE39,233 | E | 8/2006 | McGrath |
| 7,096,864 | B1 | 8/2006 | Mayer |
| 7,111,852 | B2 | 9/2006 | Woods |
| 7,117,438 | B2 | 10/2006 | Wallace |
| 7,128,709 | B2 | 10/2006 | Saruya |

(56) References Cited

U.S. PATENT DOCUMENTS

| | | |
|---|---|---|
| 7,137,951 B2 | 11/2006 | Pilarski |
| 7,193,233 B2 | 3/2007 | Smith |
| 7,216,802 B1 | 5/2007 | De La Huerga |
| 7,223,007 B1 | 5/2007 | Fredley |
| 7,234,944 B2 | 6/2007 | Nordin |
| 7,256,708 B2 | 8/2007 | Rosenfeld |
| 7,267,666 B1 | 9/2007 | Duchon |
| 7,282,029 B1 | 10/2007 | Poulsen |
| 7,315,825 B2 | 1/2008 | Rosenfeld |
| 7,336,980 B1 | 2/2008 | Kaikuranta |
| 7,360,454 B2 | 4/2008 | Kawashima |
| 7,371,214 B2 | 5/2008 | Kouchi |
| 7,386,340 B2 | 6/2008 | Schlegel |
| 7,468,032 B2 | 12/2008 | Stahmann |
| 7,469,601 B2 | 12/2008 | Sugi |
| D589,959 S | 4/2009 | Han |
| 7,516,924 B2 | 4/2009 | White |
| 7,523,040 B2 | 4/2009 | Kirchhoff |
| 7,529,083 B2 | 5/2009 | Jeong |
| 7,540,187 B1 | 6/2009 | Dillon |
| 7,566,307 B2 | 7/2009 | Inukai |
| 7,621,500 B2 | 11/2009 | Ishizaki |
| 7,751,878 B1 | 7/2010 | Merkle |
| 7,756,722 B2 | 7/2010 | Levine |
| 7,836,882 B1 | 11/2010 | Rumph |
| 7,945,452 B2 | 5/2011 | Fathallah |
| 8,027,846 B2 | 9/2011 | Schoenberg |
| 8,033,686 B2 | 10/2011 | Recker |
| 8,147,419 B2 | 4/2012 | Krauss |
| 8,233,272 B2 | 7/2012 | Fidacaro |
| 8,344,847 B2 | 1/2013 | Moberg |
| 8,398,408 B1 | 3/2013 | Hansen |
| 8,413,271 B2 | 4/2013 | Blanchard |
| 8,704,666 B2 | 4/2014 | Baker, Jr. |
| 8,931,702 B2 * | 1/2015 | Wekell et al. ............ 235/472.01 |
| 8,940,147 B1 | 1/2015 | Bartsch |
| 2001/0001179 A1 | 5/2001 | Healy |
| 2001/0018332 A1 | 8/2001 | Lustila |
| 2001/0027791 A1 | 10/2001 | Wallace |
| 2001/0034475 A1 | 10/2001 | Flach |
| 2002/0026941 A1 | 3/2002 | Biondi |
| 2002/0032386 A1 | 3/2002 | Sackner |
| 2002/0060247 A1 | 5/2002 | Krishnaswamy |
| 2002/0108011 A1 | 8/2002 | Tanha |
| 2002/0161291 A1 | 10/2002 | Kianl |
| 2002/0193679 A1 | 12/2002 | Malave |
| 2002/0196141 A1 | 12/2002 | Boone |
| 2002/0196234 A1 | 12/2002 | Gray |
| 2003/0028118 A1 | 2/2003 | Dupree |
| 2003/0029451 A1 | 2/2003 | Blair |
| 2003/0037786 A1 | 2/2003 | Biondi |
| 2003/0065536 A1 | 4/2003 | Hansen |
| 2003/0076015 A1 | 4/2003 | Ehrenreich |
| 2003/0114836 A1 | 6/2003 | Estes |
| 2003/0117296 A1 | 6/2003 | Seely |
| 2003/0120164 A1 | 6/2003 | Nielsen |
| 2003/0130590 A1 | 7/2003 | Bui |
| 2003/0135087 A1 | 7/2003 | Hickle |
| 2003/0145854 A1 | 8/2003 | Hickle |
| 2003/0171898 A1 | 9/2003 | Tarassenko |
| 2003/0191373 A1 | 10/2003 | Blike |
| 2003/0197614 A1 | 10/2003 | Smith |
| 2003/0209246 A1 | 11/2003 | Schroeder |
| 2003/0210780 A1 | 11/2003 | Pratt |
| 2003/0216621 A1 | 11/2003 | Alpert |
| 2003/0231460 A1 | 12/2003 | Moscovitch |
| 2003/0233129 A1 | 12/2003 | Matos |
| 2004/0011938 A1 | 1/2004 | Oddsen |
| 2004/0015079 A1 | 1/2004 | Berger |
| 2004/0021705 A1 | 2/2004 | Baker |
| 2004/0024303 A1 | 2/2004 | Banks |
| 2004/0032426 A1 | 2/2004 | Rutledge |
| 2004/0054261 A1 | 3/2004 | Kamataki |
| 2004/0054295 A1 | 3/2004 | Ramseth |
| 2004/0102687 A1 | 5/2004 | Brashears |
| 2004/0103001 A1 | 5/2004 | Mazar |
| 2004/0116813 A1 | 6/2004 | Selzer |
| 2004/0117209 A1 | 6/2004 | Brown |
| 2004/0118404 A1 | 6/2004 | Wallace |
| 2004/0147818 A1 | 7/2004 | Levy |
| 2004/0149892 A1 | 8/2004 | Akitt |
| 2004/0153257 A1 | 8/2004 | Munk |
| 2004/0158132 A1 | 8/2004 | Zaleski |
| 2004/0172222 A1 | 9/2004 | Simpson |
| 2004/0186357 A1 | 9/2004 | Soderberg |
| 2004/0221077 A1 | 11/2004 | Yen |
| 2004/0236192 A1 | 11/2004 | NecolaShehada |
| 2004/0249298 A1 | 12/2004 | Selevan |
| 2004/0249673 A1 | 12/2004 | Smith |
| 2005/0005932 A1 | 1/2005 | Berman |
| 2005/0010165 A1 | 1/2005 | Hickle |
| 2005/0033124 A1 | 2/2005 | Kelly |
| 2005/0033188 A1 | 2/2005 | Whitaker |
| 2005/0038332 A1 | 2/2005 | Saidara |
| 2005/0038821 A1 | 2/2005 | Wallen |
| 2005/0054920 A1 | 3/2005 | Washburn |
| 2005/0059924 A1 | 3/2005 | Katz |
| 2005/0065417 A1 | 3/2005 | Ali |
| 2005/0113650 A1 | 5/2005 | Pacione |
| 2005/0124866 A1 | 6/2005 | Elaz |
| 2005/0139213 A1 | 6/2005 | Blike |
| 2005/0146431 A1 | 7/2005 | Hastings |
| 2005/0151640 A1 | 7/2005 | Hastings |
| 2005/0177096 A1 | 8/2005 | Bollish |
| 2005/0229110 A1 | 10/2005 | Gegner |
| 2005/0251232 A1 | 11/2005 | Hartley |
| 2006/0004475 A1 | 1/2006 | Brackett |
| 2006/0022096 A1 | 2/2006 | Chan |
| 2006/0042635 A1 | 3/2006 | Niklewski |
| 2006/0058591 A1 | 3/2006 | Garboski |
| 2006/0094970 A1 | 5/2006 | Drew |
| 2006/0142808 A1 | 6/2006 | Pearce |
| 2006/0155206 A1 | 7/2006 | Lynn |
| 2006/0155589 A1 | 7/2006 | Lane |
| 2006/0199618 A1 | 9/2006 | Steer |
| 2006/0226992 A1 | 10/2006 | Al-Ali |
| 2006/0258926 A1 | 11/2006 | Ali |
| 2006/0280621 A1 | 12/2006 | Kinugawa |
| 2007/0007418 A1 | 1/2007 | Lubbers |
| 2007/0028921 A1 | 2/2007 | Banner |
| 2007/0032749 A1 | 2/2007 | Overall |
| 2007/0044578 A1 | 3/2007 | Jones |
| 2007/0051861 A1 | 3/2007 | Teramachi |
| 2007/0060869 A1 | 3/2007 | Tolle |
| 2007/0093784 A1 | 4/2007 | Leonard |
| 2007/0100213 A1 | 5/2007 | Dossas |
| 2007/0107728 A1 | 5/2007 | Ricciardelli |
| 2007/0108291 A1 | 5/2007 | Bhatia |
| 2007/0120763 A1 | 5/2007 | De Paepe et al. |
| 2007/0176931 A1 | 8/2007 | Tivig |
| 2007/0180140 A1 | 8/2007 | Welch |
| 2007/0199388 A1 | 8/2007 | Furkert |
| 2007/0255116 A1 | 11/2007 | Mehta |
| 2007/0265533 A1 | 11/2007 | Tran |
| 2007/0276277 A1 | 11/2007 | Booth |
| 2008/0033254 A1 | 2/2008 | Kamath |
| 2008/0039701 A1 | 2/2008 | Ali |
| 2008/0051667 A1 | 2/2008 | Goldreich |
| 2008/0103375 A1 | 5/2008 | Kiani |
| 2008/0154909 A1 | 6/2008 | Dam |
| 2008/0167569 A1 | 7/2008 | Ermes |
| 2008/0170287 A1 | 7/2008 | Champion |
| 2008/0177160 A1 | 7/2008 | Al Ali |
| 2008/0177397 A1 | 7/2008 | Davlin |
| 2008/0181465 A1 | 7/2008 | Sauerwein |
| 2008/0221418 A1 | 9/2008 | Al-Ali |
| 2008/0221495 A1 | 9/2008 | Steffens |
| 2008/0228089 A1 | 9/2008 | Cho |
| 2008/0249376 A1 | 10/2008 | Zaleski |
| 2008/0251003 A1 | 10/2008 | Boston |
| 2008/0267790 A1 | 10/2008 | Gaudet |
| 2008/0271736 A1 | 11/2008 | Leonard |
| 2008/0275309 A1 | 11/2008 | Stivoric |
| 2008/0281168 A1 | 11/2008 | Gibson |

(56) References Cited

U.S. PATENT DOCUMENTS

| | | |
|---|---|---|
| 2008/0281170 A1 | 11/2008 | Eshelman |
| 2008/0287763 A1 | 11/2008 | Hayter |
| 2008/0294057 A1 | 11/2008 | Parlikar |
| 2008/0310600 A1 | 12/2008 | Clawson |
| 2008/0319331 A1 | 12/2008 | Zizzo |
| 2009/0005703 A1 | 1/2009 | Fasciano |
| 2009/0015116 A1 | 1/2009 | Arceta |
| 2009/0024008 A1 | 1/2009 | Brunner |
| 2009/0054743 A1 | 2/2009 | Stewart |
| 2009/0055735 A1 | 2/2009 | Zaleski |
| 2009/0069642 A1 | 3/2009 | Gao |
| 2009/0076345 A1 | 3/2009 | Manicka |
| 2009/0099480 A1 | 4/2009 | Salgo |
| 2009/0117784 A1 | 5/2009 | Wu |
| 2009/0124239 A1 | 5/2009 | Tsuei |
| 2009/0131805 A1 | 5/2009 | O'Brien |
| 2009/0133609 A1 | 5/2009 | Nethken |
| 2009/0149901 A1 | 6/2009 | Jayne |
| 2009/0151720 A1 | 6/2009 | Inoue |
| 2009/0182204 A1 | 7/2009 | Semler |
| 2009/0192541 A1 | 7/2009 | Ortiz |
| 2009/0193315 A1 | 7/2009 | Gower |
| 2009/0200902 A1 | 8/2009 | McKay |
| 2009/0206713 A1 | 8/2009 | Vilkas |
| 2009/0209849 A1 | 8/2009 | Rowe |
| 2009/0237264 A1 | 9/2009 | Bobey |
| 2010/0004539 A1 | 1/2010 | Chen |
| 2010/0007588 A1 | 1/2010 | Zygmunt |
| 2010/0014229 A1 | 1/2010 | Horie |
| 2010/0056875 A1 | 3/2010 | Schoenberg |
| 2010/0070417 A1 | 3/2010 | Flynn |
| 2010/0073915 A1 | 3/2010 | Nittou |
| 2010/0094096 A1 | 4/2010 | Petruzzelli |
| 2010/0110019 A1 | 5/2010 | Ozias |
| 2010/0137729 A1 | 6/2010 | Pierry |
| 2010/0164452 A1 | 7/2010 | Ruan |
| 2010/0175695 A1 | 7/2010 | Jamison |
| 2010/0179400 A1 | 7/2010 | Brauker |
| 2010/0233891 A1 | 9/2010 | Broeksteeg |
| 2010/0238138 A1 | 9/2010 | Goertz |
| 2010/0259881 A1 | 10/2010 | Choi |
| 2010/0261979 A1 | 10/2010 | Kiani |
| 2010/0285771 A1 | 11/2010 | Peabody |
| 2010/0294405 A1 | 11/2010 | Longinotti-Buitoni |
| 2010/0298656 A1 | 11/2010 | McCombie |
| 2010/0298718 A1 | 11/2010 | Gilham |
| 2010/0324380 A1 | 12/2010 | Perkins |
| 2010/0324384 A1 | 12/2010 | Moon |
| 2011/0004071 A1 | 1/2011 | Faiola |
| 2011/0071420 A1 | 3/2011 | St. Pierre |
| 2011/0088694 A1 | 4/2011 | Tobia |
| 2011/0130798 A1 | 6/2011 | Elghazzawi |
| 2011/0138323 A1 | 6/2011 | Skidmore |
| 2011/0152629 A1 | 6/2011 | Eaton |
| 2011/0164074 A1 | 7/2011 | Frank |
| 2011/0225771 A1 | 9/2011 | Bartnick |
| 2011/0245579 A1 | 10/2011 | Bruggeman |
| 2011/0257489 A1 | 10/2011 | Banet |
| 2011/0279383 A1 | 11/2011 | Wilson |
| 2011/0279958 A1 | 11/2011 | Clark |
| 2012/0030610 A1 | 2/2012 | DiPerna |
| 2012/0075327 A1 | 3/2012 | Mackenzie |
| 2012/0095778 A1 | 4/2012 | Gross |
| 2012/0105233 A1 | 5/2012 | Bobey |
| 2012/0105774 A1 | 5/2012 | Fletcher |
| 2012/0127103 A1 | 5/2012 | Qualey |
| 2012/0209984 A1 | 8/2012 | Gonzalez-Banos |
| 2012/0232398 A1 | 9/2012 | Roham |
| 2013/0267861 A1 | 10/2013 | Vassallo |

FOREIGN PATENT DOCUMENTS

| | | |
|---|---|---|
| EP | 0686900 A2 | 12/1995 |
| EP | 1054338 | 11/2000 |
| EP | 1227752 A1 | 8/2002 |
| EP | 1852060 | 11/2007 |
| GB | 2389290 A | 12/2003 |
| JP | 07163527 | 6/1995 |
| JP | 2003210422 | 7/2003 |
| WO | 9415523 | 7/1994 |
| WO | 9918705 | 4/1999 |
| WO | 03091841 | 11/2003 |
| WO | 03102850 | 12/2003 |
| WO | 2006094055 A2 | 9/2006 |
| WO | 2010126916 | 11/2010 |
| WO | 2010126916 A1 | 11/2010 |
| WO | 2011001302 A1 | 1/2011 |
| WO | 2011046636 A1 | 4/2011 |
| WO | 2011047363 A1 | 4/2011 |
| WO | 2011119512 A1 | 9/2011 |
| WO | 2012068564 A2 | 5/2012 |
| WO | 2012068565 A2 | 5/2012 |
| WO | 2012068567 | 5/2012 |
| WO | 2012068568 A2 | 5/2012 |
| WO | 2012083276 A2 | 6/2012 |
| WO | 2012083281 A1 | 6/2012 |
| WO | 2012125135 A1 | 9/2012 |
| WO | 2012128808 A2 | 9/2012 |
| WO | 2012158720 A1 | 11/2012 |
| WO | 2013056171 A2 | 4/2013 |
| WO | 2013173520 A2 | 11/2013 |
| WO | 2013173521 A2 | 11/2013 |
| WO | 2014055660 A1 | 4/2014 |
| WO | 2014194193 | 12/2014 |

OTHER PUBLICATIONS

Notice of Allowance dated Sep. 3, 2014 for U.S. Appl. No. 13/973,862.
Office Action dated Aug. 28, 2009 for U.S. Appl. No. 11/716,513.
Office Action dated Mar. 23, 2010 for U.S. Appl. No. 11/716,513.
Office Action dated Aug. 1, 2011 for U.S. Appl. No. 11/716,513.
Office Action dated Jul. 2, 2012 for U.S. Appl. No. 11/716,513.
International Search Report for PCT/US2013/063087, Mar. 6, 2014.
Supplementary European Search Report, Nov. 25, 2009, Spacelabs Medical, PCT/US2006/007269.
Schoenberg, Roy, MD; Sands, Daniel Z., MD MPH; Safran Charles, MD; Center for Clinical Computing, Beth Israel Deaconess Medical Center, Harvard Medical School, "Making ICU Alarms Meaningful: a comparison of traditional vs. trend-based algorithms" (AMIA '99 Annual Symposium), 1999, pp. 1-5.
International Search Report for PCT/US06/07269, Aug. 28, 2006.
International Preliminary Report on Patentability, PCT/US2006/007269, Sep. 11, 2007, Spacelabs Medical.
Notice of Allowance dated Oct. 31, 2014 for U.S. Appl. No. 12/114,689.
International Search Report for PCT/US10/32635, Jul. 23, 2010.
Office Action dated Feb. 26, 2015 for U.S. Appl. No. 12/768,714.
Office Action dated Aug. 14, 2014 for U.S. Appl. No. 12/768,714.
Office Action dated Nov. 21, 2013 for U.S. Appl. No. 12/768,714.
Office Action dated Jun. 18, 2012 for U.S. Appl. No. 12/768,714.
Office Action dated Jan. 17, 2013 for U.S. Appl. No. 12/768,714.
Office Action dated Dec. 10, 2014 for U.S. Appl. No. 14/165,193.
Office Action Dated May 31, 2013 for U.S. Appl. No. 13/052,883.
International Search Report for PCT/US2011/029278, Aug. 2, 2011.
International Search Report for PCT/US2011/61557, Apr. 23, 2012.
International Search Report for PCT/US2011/061554, Feb. 14, 2014.
International Search Report for PCT/US2011/061555, Apr. 17, 2012.
International Search Report for PCT/US2011/061558, Aug. 10, 2012.
International Preliminary Report on Patentability for PCT/US2011/061554, Feb. 25, 2014.
IntelliVue Patient Monitor; MP20/30, MP40/50, MP60/70/80/90, Release G.0 with Software Revision G.0x.xx (PHILIPS) Sep. 2008; pp. 4, 10, 19, 20, 46-49, 82, 326, 348, 420, 424, 452; Accessed on Sep. 30, 2013: <http://www.mc.vanderbilt.edu/documents/nursing-educationresources/files/MP20-MP90%20Instructions%20for%20Use%20Manual%20Rev_G_0%20%20English%20M8000-9001K.pdf>.

(56) References Cited

OTHER PUBLICATIONS

Office Action dated Nov. 12, 2014 for U.S. Appl. No. 13/300,462.
Notice of Allowance dated Jan. 28, 2015 for U.S. Appl. No. 13/300,478.
International Search Report, PCT/US2011/028007, Jul. 11, 2011, International Search Authority.
International Preliminary Report on Patentability, PCT/US2011/028007, Sep. 17, 2013, International Search Authority.
Office Action dated Nov. 21, 2014 for U.S. Appl. No. 13/045,539.
International Preliminary Report on Patentability, PCT/US12/38000, Nov. 13, 2013.
International Search Report for PCT/US12/38000, Oct. 23, 2012.
International Search Report for PCT/US10/34025, Aug. 9, 2010.
Notice of Allowance dated Mar. 13, 2015 for U.S. Appl. No. 12/906,081.
International Search Report for PCT/US2012/060125, Apr. 19, 2013.
International Search Report for PCT/US2010/052977, Mar. 18, 2011.
International Search Report for PCT/US2011/065676, Sep. 20, 2012.
International Search Report for PCT/US2011/065678, Jun. 29, 2012.
International Search Report, PCT/US2011/065685, May 8, 2012, International Search Authority.
International Preliminary Report on Patentability, PCT/US2011/065678, Jun. 18, 2013, International Search Authority.
International Preliminary Report on Patentability, PCT/US2011/065685, Jun. 18, 2013.
Office Action dated Sep. 22, 2014 for U.S. Appl. No. 13/329,186.
Notice of Allowance dated Jan. 8, 2015 for U.S. Appl. No. 13/329,259.
International Search Report for PCT/US2014/040225, Nov. 5, 2014.
Notice of Allowance dated May 27, 2015 for U.S. Appl. No. 14/165,193.
Supplemental Notice of Allowance dated Apr. 20, 2015 for U.S. Appl. No. 12/906,081.
Notice of Allowance dated May 11, 2015 for U.S. Appl. No. 13/300,462.
Office Action dated May 21, 2015 for U.S. Appl. No. 13/300,526.
Office Action dated Jun. 18, 2015 for U.S. Appl. No. 13/329,186.
Office Action dated Jul. 2, 2015 for U.S. Appl. No. 13/895,527.
European Search Report for EP12786443.7, Apr. 15, 2015.
Office Action dated Apr. 7, 2015 for U.S. Appl. No. 13/472,332.
Partial European Search Report for EP 12839321.2, May 26, 2015.

* cited by examiner

HEALTH DATA COLLECTION TOOL

TECHNICAL FIELD

This invention relates to the field of health care devices for gathering, displaying and transmitting health care data concerning the vital signs of a patient, particularly to portable nursing devices for gathering such data, and still more particularly to portable devices that provide for assimilating a plurality of different types of health care data, including patient identity, using a single integrated device.

BACKGROUND OF THE INVENTION

In a medical facility such as a hospital, clinic or doctor's office, the creation and maintenance of patient files is critical to recording vital data and history of a patients treatment. Patient files include patient identifying information as well as a variety of health care data associated with the patient. Identifying information is routinely taken at intake of a patient and typically includes, for example, name, age, sex and insurance information, which is used to establish the base file for the patient. In addition, routine health care data such as temperature, pulse, blood pressure and the like are typically hand recorded at or near intake and included in a hard-copy paper file. The file is typically physically transferred to a patient examination room where further health care data and notes may be entered by a health care provider and manually recorded into the file.

If the patient is to be admitted to a hospital, an identification bracelet is typically created to be worn on the patient's wrist for follow-up care, and the patient's file is transferred to the patient's bedside. At the bedside, the file is manually updated upon periodic visits by a physician or nurse who manually records notes and other health care data into the file. Prescription and diagnosis information is also recorded in the file. In instances before or after a significant medical procedure such as birth or surgery, basic vital signs such as temperature, pulse, blood pressure, respiratory rate, oximetry, electrocardiogram (ECG) or other data pertaining the patient's body may be continuously monitored during the patient's stay. Specialized semi-portable monitoring instruments for obtaining and monitoring this type of health care data are part of a hospital's inventory of equipment that is assigned to individual patients on an as-needed basis and rolled into a patient's room on carts or roller stands. A large variety of semi-portable monitors are commercially provided by numerous manufacturers and distributors.

Fully portable devices that do not require a cart or stand are also commercially available. One example of a fully portable data health care data device provided by WelchAllyn is the SPOT VITAL SIGNS™ device that allows a health care provider to take non-invasive blood pressure, pulse, oximetry, and arterial pressure data, and which may be configured with a printer for recording the data. On routine visits, or "rounds," hard copy recordings of health care data obtained from such devices may be periodically printed and included in the files to create a vital signs history. Alternatively, the health care provider may manually record such data in the file with time and date information.

In the past, day-to-day patient intake and monitoring information was exclusively hand recorded in a paper file by a variety of health care provider personnel. Today, health care institutions are increasingly moving toward recording health care information in electronic patient files rather than in hard-copy files. In typical electronic file systems, patient files are maintained on a centralized computer system and patient information and health care data are entered from a variety of distributed smart terminals positioned in intake rooms, examination rooms and hospital rooms. The smart terminals serve as a substitute for the hard copy files, permitting the variety of health care providers to enter and display a variety of health care information from a variety of locations without need for physically transferring the hard copy file.

Another improvement in recent years is that monitoring devices have been equipped with telemetry equipment to wirelessly upload health care data through a network of receivers that are positioned remotely from the monitors. In certain situations, such as with ambulatory patients requiring continuous monitoring of specific vital signs, or with ambulance patients being transported to a hospital under emergency situations, small, portable monitors with self-contained power and data telemetry units are used to continuously record and transmit health care data to a centralized computer system. Commercially available examples of such portable monitors are exemplified by the Micropaq™ and Propaq™ monitors provided by WelchAllyn. These monitors display ECG waveforms, heart rate, invasive or non-invasive blood pressure, temperature, pulse oximetry and respiratory data. In certain optional configurations, these devices can wirelessly transmits such data over a local area wireless radio frequency network (FlexNet™). In other configurations, data assimilated by the monitors may be transmitted via infrared data transmission.

While the provision of centralized electronic patient record files and portable health care data monitors equipped with telemetry options has improved the ease and efficiency of collecting, transmitting and storing health care data, there remains a need in the art to equip a health care provider with options for integrating the collected data with patient identification information, and for providing for additional types of data that can be collected using an inexpensive and fully portable device.

SUMMARY OF THE INVENTION

The invention provides a portable, multifunctional health data tool for use by a healthcare provider. The health data tool includes a housing configured to be of a shape, size and weight to permit the housing to be held in a hand of a health-care provider. It further contains a code reader associated with the housing configured to read coded information, such as information pertaining to the patient's identity or information pertaining to a drug or device used by the patient. The tool further includes multiple input ports for different data assimilation devices associated with the housing for inputting different health care data obtained from a patient into the health data tool. A display screen configured to display the health care data obtained from the data assimilation devices is also provided. Finally, the tool includes a data transmitter and a data receiver port to permit the health care data and other information to be transferred between the health data tool and a remote device that is separate from the tool.

In one aspect, the code reader is a bar code scanner that reads bar code information. In another aspect, the code reader is a radio receiver that that receives a radio signal encoding the information. In another embodiment, the code reader is an optical character recognition device that reads character information. In yet another embodiment, the code reader recognizes a pattern of dots encoding the information.

In another aspect, the housing comprises an upper portion that houses the display screen and a lower portion downwardly extending from the upper portion that defines a handle dimensioned to fit within the hand of the health care provider.

The housing may include a plurality of storage compartments to store the plurality of data assimilation devices associated with the housing. A plurality of doors providing access to the storage compartments may also be provided to enclose the associated data assimilation devices within the health data tool. In most embodiments, at least one of the storage compartments should include a compartment for holding a blood pressure cuff. The blood pressure cuff storage compartment may, for example, be configured as a slot within the housing. In other embodiments, at least one of the data assimilation devices, such as the blood pressure cuff, is removably attachable to the housing by a spring actuated latch. The housing may be configured to store an air compressor for operating the blood pressure cuff, or the blood pressure cuff may be manually operated by a hand pump.

The health data tool further includes an electronic memory associated with the housing to store the health care data. The electronic memory may be configured to store health care data for a plurality of patients, typically in a database format.

In the following detailed description of exemplary embodiments of the invention, reference is made to the accompanying drawings, which form a part hereof, and in which are shown, by way of illustration, specific exemplary embodiments in which the invention may be practiced. In the drawings, like numerals describe substantially similar components throughout the several views. These embodiments are described in sufficient detail to enable those skilled in the art to practice the invention. Other embodiments may be utilized and structural, logical, electrical, and other changes may be made without departing from the spirit or scope of the present invention. The following detailed description is, therefore, not to be taken in a limiting sense, and the scope of the present invention is defined only by the appended claims.

DETAILED DESCRIPTION OF PREFERRED EMBODIMENTS

As used herein, "health care data" is the meaningful form of data, including at least in-part, data commonly known as "vital signs" that pertain to the health of a patient. Typical types of health care data include, but are not limited to, temperature, pulse, blood $O_2$ level, electro cardiogram data, blood pressure, respiratory rate, appearance (such as may be recorded by a camera), sound information (such as obtained by a stethoscope) and the like.

The term "patient identifying data" refers to data that can be used to identify a patient. Typical types of patient identifying data includes name, age, sex, and insurance information.

The term "signal data" refers to the raw signal that is received from a health care data assimilation device before the raw signal is converted into meaningful health care data by the action of a microprocessor. Typically, signal data is in the form of an amplitude or a frequency of a voltage, a current, or optical analogues of the same, which has been transduced from a detector that detects changes in pressure, light, sound, temperature or other measurable attribute.

The term "associated with" as used with respect to a component part of the health data tool (described in more detail hereafter) means that the component part is physically stored in, attached, or coupled or connected to the health data tool. The attachment or connection may be fixed or removable.

Figure 1:
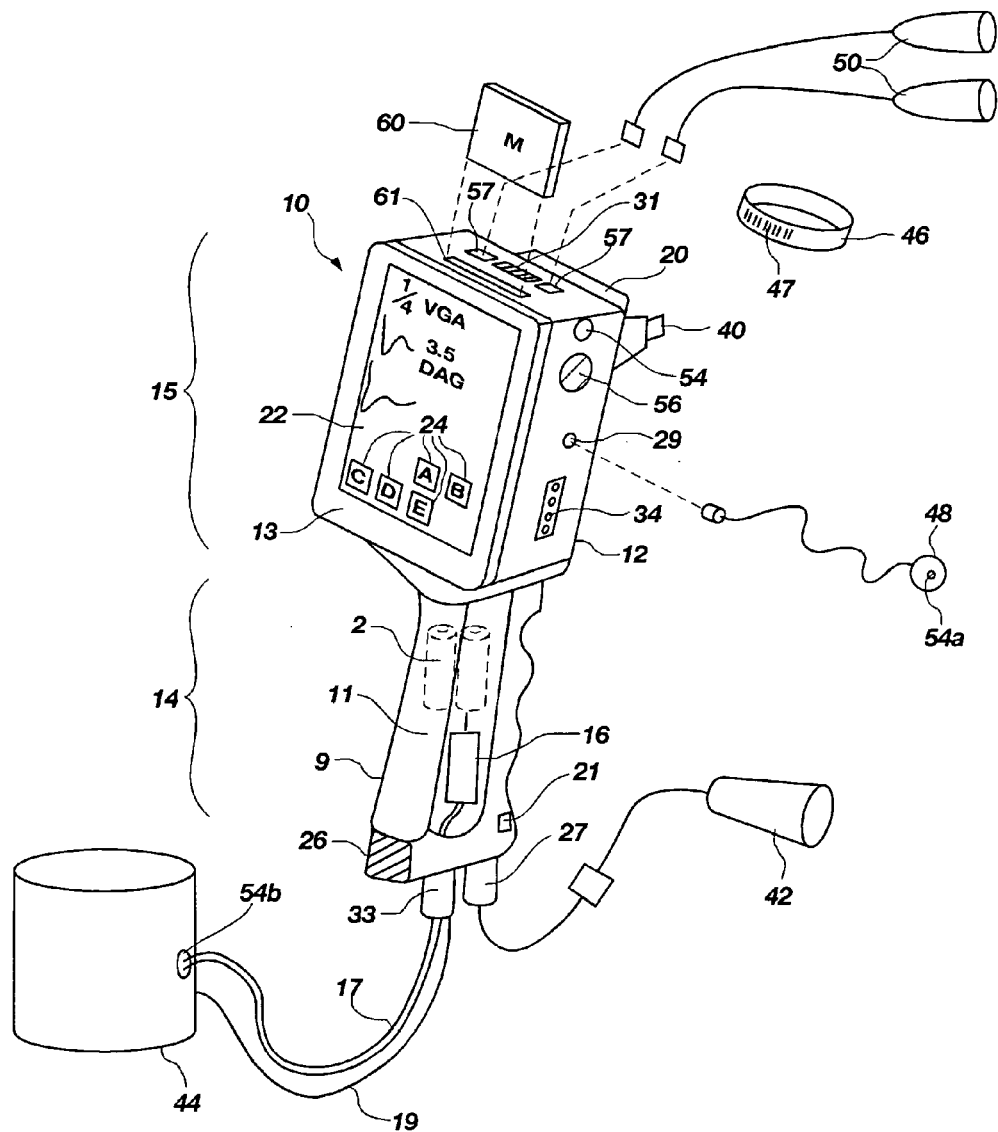
FIG. 1 is a front isometric view of an exemplary embodiment of the health data tool of the invention including exemplary data assimilation devices associated therewith.
Figure 2:
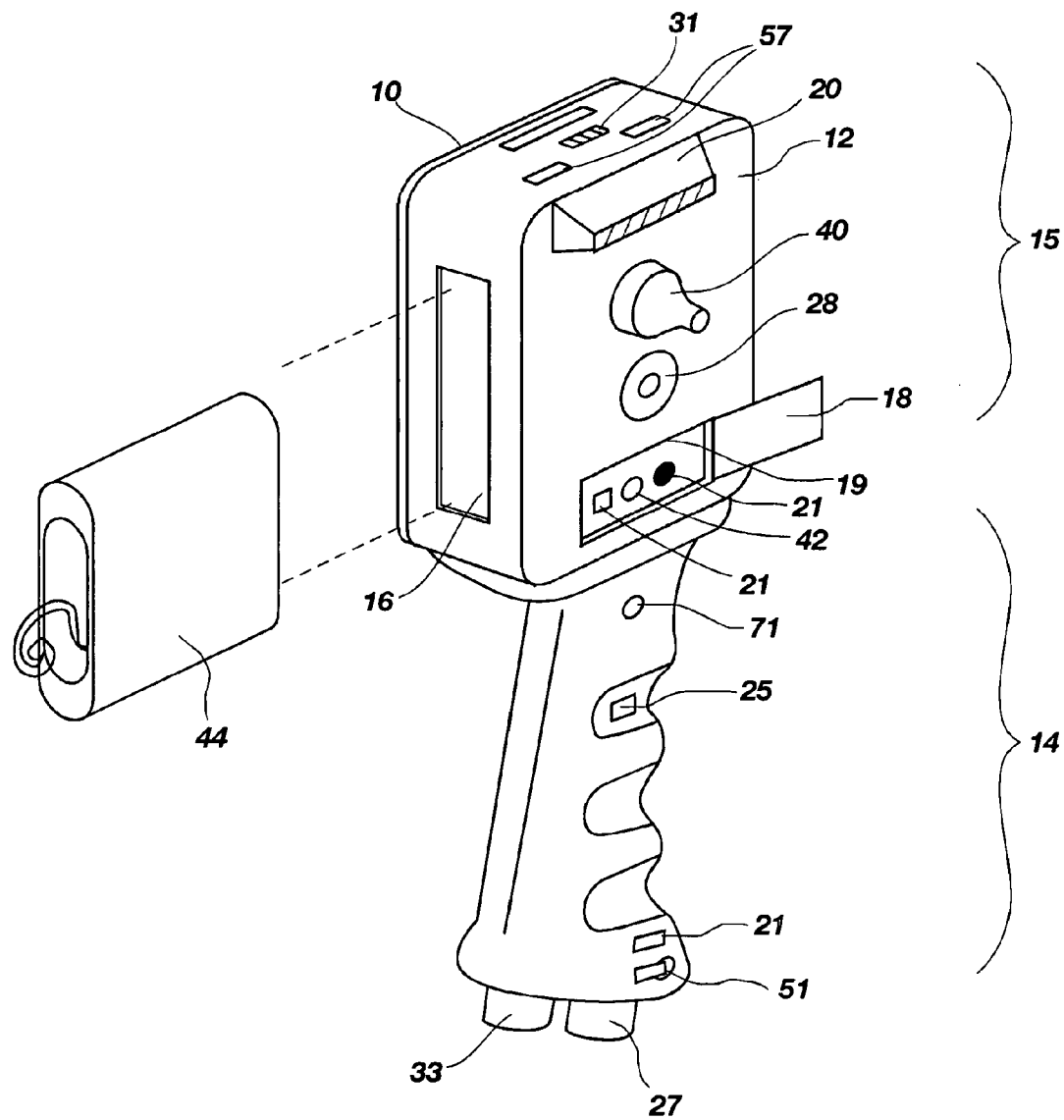
FIG. 2 is a rear isometric view of an exemplary embodiment of the health data tool of the invention.

FIGS. 1 and 2, illustrate front and rear isometric views, respectively, of one embodiment of a health data tool 10 of the invention. The health data tool 10 includes a housing 12 that houses a plurality of data assimilation devices 40, 42, 44, 48, 50, 57 associated with health data tool 10. The housing 12 includes a lower handle 14 portion, which in advantageous embodiments, extends longitudinally downward with respect to a front display surface 13 of the housing 12. The housing 12 is configured to be of shape, size and weight to permit the health data tool 10 to be held in one hand of health care provider. In typical embodiments, the housing 12 is made of a plastic material and occupies less than about 2 or less than about 1 cubic feet of space and weighs less than about 10 pounds, less than about 5 pounds or less than about 3 pounds. The downwardly extending handle 14 and overall configuration of the health data tool 10 permits a health care provider to hold the health data tool 10 in one hand while manipulating data assimilation devices with the other hand and simultaneously observing data that is displayed on a display screen 22 located in an upper portion 15 of the housing 12. The data assimilation devices 40, 42, 44, 48, 50, 57 and the display screen 22 are described in more detail hereafter.

In certain embodiments, the downwardly extending handle 14 is configured with an access door 9 that provides access to a hollow compartment 11. The hollow compartment 11 may be used to store one or more of the data assimilation devices. In the embodiment depicted in FIG. 1, the hollow compartment 11 in the handle 14 encloses batteries 13 used to power the health data tool 10 and, optionally, one or more of the data assimilation devices associated therewith. As depicted in FIG. 1, the hollow compartment 11 also houses a small air compressor 16 used to supply air through an air line 17 for automatic operation of a non-invasive blood pressure cuff 44. Of course, the batteries or air compressor 16 may be located elsewhere in the housing 12 so long as suitable electrical connections or tubing is provided to power the health data tool 10 and channel air flow to the air line 17. The air compressor 16 is not needed when the blood pressure cuff 44 is configured for manual inflation using a bulb.

The health data tool 10 includes a code reader 20 associated with the housing 12 to read information pertaining to the patient. In advantageous embodiments, the code reader 20 is integrated into the housing 12, although in other embodiments the code reader 20 may detachably coupled to the housing 12. The function of the code reader 20 is to read coded information associated with or pertaining to the patient. The coded information typically includes personal information that identifies the patient and may also include information pertaining to drugs or devices that are to be administered or otherwise used in treating or monitoring the patient.

In one exemplary embodiment, the code reader 20 is a standard bar code reader. Typically, during an intake procedure at a health care facility a patient to be treated or admitted is supplied with an identity tag 46, usually in the form of wrist bracelet, that includes the name of the patient, the date of admission, the administering health care provider or other information such as insurance provider and the like. Some or all of this information may be encoded in a bar code 47 on the identity tag 46. The bar code reader 20 permits this identifying information to be rapidly and accurately entered into the health data tool 10.

The patient may also be prescribed a drug therapy that includes a name for the prescribed drug, a dosage and frequency of administration. In certain cases the patient may bring a drug container to a health care provider upon admission to a health care facility to assist in diagnosis or treatment, while in other cases the health care provider at the facility may prescribe a drug treatment to the patient. Such prescription information, or parts thereof, may also be encoded in a bar code associated with the container that contains the drug. The bar code reader 20 permits the health care provider to enter the relevant drug information into the health data tool 10. Similarly, an admitted patient may be assigned usage of various medical devices from an inventory of devices provided by the health care facility. These medical devices often include a bar code to identify the particular device for tracking, performance monitoring and inventory purposes. The bar code reader 20 allows the health care provider to associate a given medical device with a given patient identification in a memory record to facilitate these purposes.

While the bar code reader 20 may be the most universally adopted form of a code reader 20, it is understood that that many other embodiments of the code reader 20 may be associated with the health data tool 10 to provide the same or similar functions. Another embodiment of the code reader 20, for example, is a "dot" reader that scans a pattern of dots that encode information. Another embodiment is an optical character recognition scanner that scans an image in bit form and then converts the scanned image into alphanumeric characters. Another embodiment is a magnetic strip reader that extracts information magnetically encoded on a data strip. Yet another embodiment is a radio frequency (RF) receiver that receives electromagnetic waves transmitted from an RF identification tag in which information regarding the subject is encoded. Sill another embodiment of the code reader 20 is a hologram reader that detects spectral or diffraction patterns emitted by an illuminated hologram and extracts information encoded therein form the pattern of spectral or diffraction patterns detected. Accordingly, the skilled person will understand that the code reader 20 can be embodied in many forms and with many variations, as long as the code reader 20 permits information to be extracted from a tag, card or other identifying device associated with a subject patient (or thing).

Turning now to the data assimilation devices 40, 42, 44, 48, 50, and 57, in various embodiments, the data assimilation devices associated with the health data tool 10 include at least two different instruments for measuring health care data from a patient. Example data assimilation devices include, but are not limited to, a pulse oximeter (SPO2 meter) 42 for measuring pulse rate and oxygen saturation of the blood, a thermometer such as tympanic thermometer 40 for measuring a patient's temperature, a non-invasive blood pressure device 44 that includes a blood pressure cuff for measuring blood pressure, an electronic stethoscope 48 for detecting interior sounds from the patients body, and a "two finger" electrocardiogram device 57 or an ECG lead wire set 50 for recording cardiac activity thorough finger electrodes. In some advantageous embodiments, the health data tool 10 also includes a digital camera 28 as a data assimilation device integrated within the housing 12 for recording digital pictures of the patient.

The housing 12 of the health data tool 10 also includes one or more device input ports 27, 29, 31 33, and 34 configured to receive data output from the data assimilation devices. 40, 42, 44, 48, 50, and 57. In certain examples, the input ports 29, 31 and 33 are particularly configured to receive output from the data communication lines of particular data assimilation devices such as the stethoscope 48, the ECG 50 and the blood pressure cuff 44, respectively. Blood pressure input port 33 may be further configured for delivering air pressure to the blood pressure cuff 44 through air flow line 17 and to receive data from the blood pressure cuff 44 through data input line 19. The input ports 34 may also be configured to receive data output from the ECG lead wire set 50. The input port 27 is a standard two-way input/output computer interface port that receives a standard computer data communication cable, such as for example, a USB cable. Various commercially available data assimilation devices, exemplified by the SPO2 oximeter 42 depicted in FIG. 1, may be pre-configured or adapted to output data over such standard computer cables. One advantage of the two-way input/output port 27 is that it can be used to receive data from the data assimilation devices in one operational mode of the health data tool 10, and used as a data transmitter or receiver port in another operational mode where the health care data is uploaded or downloaded into a remote computer system as will be described in more detail hereafter.

As illustrated in FIG. 2, the housing 12 also includes one or more storage compartments 16 and 19 for storing the data assimilation devices associated with health data tool 10. The storage compartment 16 is an open slot configured for storing the blood pressure cuff 44 folded or rolled into a size that slips into the slot 16. The storage compartment 19 is configured to store one or more smaller data assimilation devices, exemplified in FIG. 1 by SPO2 pulse oximeter 42. The interior of storage compartments 16 or 19 may optionally be equipped with clamps, hooks, Velcro™ or other latching mechanism 21 for securely holding the data assimilation device within the storage compartment 16 or 19. In addition, or alternatively, the storage compartment 19 may be configured with a door 18 for enclosing the interior of the compartment 19 with the stored data assimilation device. The door 18 in various embodiments, may be sliding door, a swinging door, or a removable door.

Figure 3:
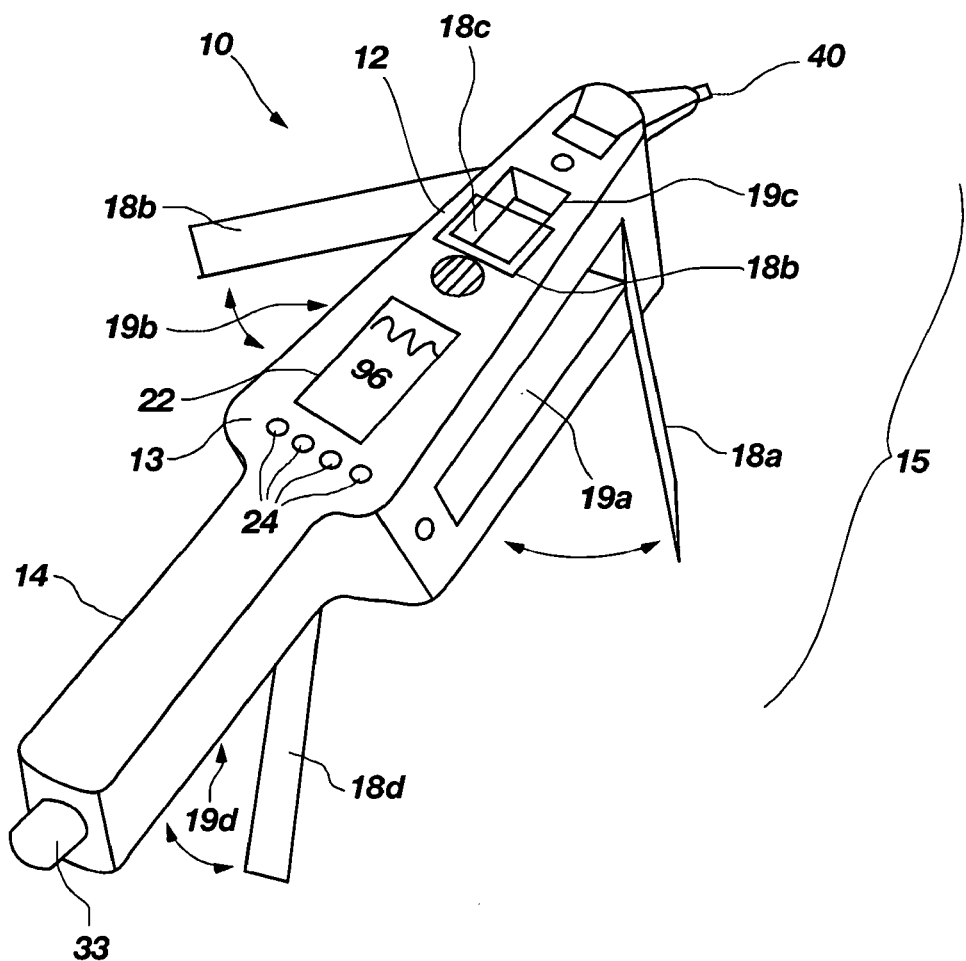
FIG. 3 is a front isometric view of another exemplary embodiment of a health data tool of the invention illustrating storage compartments incorporated into the health data tool.

FIG. 3 illustrates another configuration of the health data tool 10 and depicting other locations of various storage compartments 19a and 19b with corresponding access doors 18a and 18b, which are located on side edges of the upper portion 15 of the housing 12. Storage compartment 19c with sliding door 18c is located on the upper surface 13 of the health data tool along with the display screen 22. Storage compartment 19d with corresponding access door 18d is located on the back side of downwardly extending handle 14. Accordingly, the storage compartments 16 and 19 may be located anywhere in the housing 12 where there is room to accommodate a compartment without making the overall dimensions of the health data tool 10 too large to be comfortably handled by a health care provider.

Figure 4:
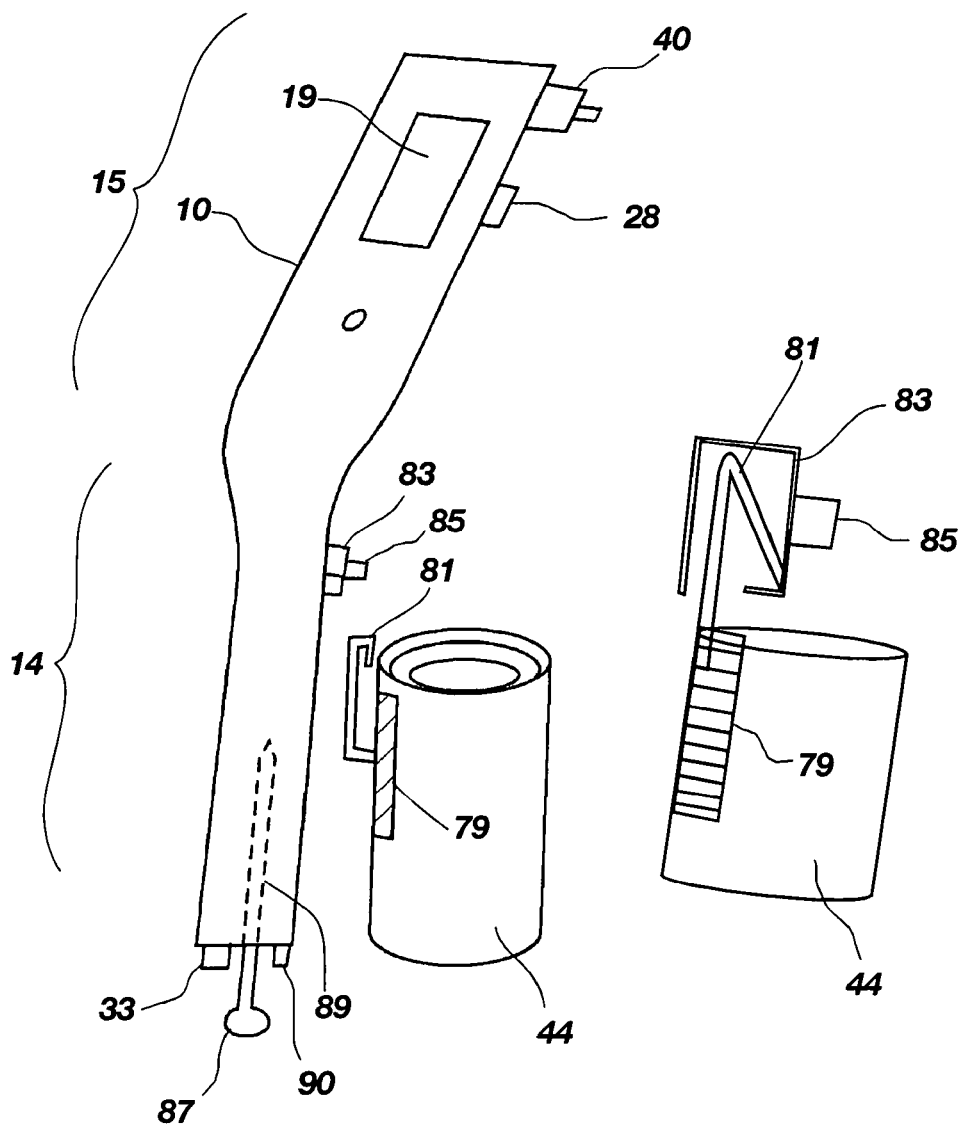
FIG. 4 is a side elevational view of an exemplary embodiment depicting device attachment clips.

The storage compartments 16 and 19 represent one example embodiment of means to associate the data assimilation devices with the health data tool 10 of the invention. Other means are also available. For example FIG. 4 is a side view of an alternative means for associating data assimilation devices 44 and 87 with the health data tool 10. In this embodiment, a thermistor type temperature probe 87 that is separate from the tympanic thermometer 40 is releasably inserted into a receptacle 89 situated in the handle 14 of the housing 12. The temperature probe 87 is secured within, and released from, the receptacle 89 by means of closing and opening a latch mechanism 90 provided on the bottom of the handle 14. Also in this embodiment, instead of using a slot 16 or compartment 18 to store the blood pressure cuff 44, the cuff 44 is rolled and banded with an elastic or Velcro™ band 79. The band 79 is attached to a flat spring clip 81 configured to be inserted into a spring receptacle 83 that securely holds the blood pressure cuff 44 in place on the handle 14 of the health data tool 10 by the tension of the spring clip 81 against the wall and ledge of the spring receptacle 83. The blood pressure cuff 44 is released from the spring receptacle 83 by operation of spring release mechanism 85, which compresses the flat spring clip 81 thereby releasing the tension of the spring from the walls and ledge of the receptacle.

Referring again to FIG. 1, in some advantageous embodiments, the health data tool 10 optionally includes a microphone 54 for collecting sound information. The sound information may include for example, oral notes made by a health care provider or patient or sounds emitted from the patients body, such as the sound of a heartbeat, organ function or flow of blood. Specialized microphones 54a or 54b may be configured with the stethoscope 48 or the blood pressure device 44 to amplify the sound of the patient's heartbeat, organ function or blood flow. A speaker 56 and associated amplifier (not shown) may optionally be associated with the health data tool to audibly emit the sounds received from the microphones 54, 54a or 54b.

The front surface 13 of the health data tool 10 also includes input keys 24 for selecting various functions to be executed by the health data tool 10. The input keys 24 may be touch-screen type input keys as depicted in FIG. 1 or conventional toggle input keys 24 integrated into the housing 12 separately from the display screen 22, as depicted in FIGS. 3-6. The display screen 22 is configured to display a plurality of different types of health care data obtained by the data assimilation devices and to display commands or status information selected by the input keys 24. In various embodiments the display screen 22 displays wave form data, alpha numeric data and/or image data.

In an example use, input key 24a is depressed to select a particular data assimilation device to acquire health care data. A name or other designation of the selected device is initially displayed on the display screen 22 to verify the selection. Toggling of the input key 24A sequentially displays the name of different input devices. The selected device is activated by the health care provider and the health data tool 10 is set to acquire and display the selected type of data by depressing enter key 24B. Alternatively, the input ports 27, 29, 31 and 33 may be configured with a plug-and-play type of switch to automatically set the health data tool for acquiring data from a particular data assimilation device when that device is plugged into the appropriate input port. The health care provider then withdraws the necessary data assimilation device from its storage location in the housing 12 and, in the case of data assimilation devices such as the blood pressure cuffs 44, the SPO2 pulse oximeter 42 or finger ECG electrodes 57, dons the instrument on the patient. Alternatively, in the case of data assimilation devices such as the stethoscope 48, thermometer 40, or camera 28, the health care provider situates the instrument in the appropriate location to acquire the health care data.

Once donned or situated, the health care provider presses input button 24c to begin acquiring the health care data. In the case of a camera 28, the selection of that device activates trigger 25 to function as a shutter release so that when the trigger 25 is depressed, the camera takes a photo. In any case, the acquired data is displayed on display screen 22 in the appropriate form for the selected device. For example, if the selected data assimilation device is the two-finger ECG 57 or ECG lead wire set 50, then the wave form of the electrocardiogram signal is displayed on the display screen 22. If the selected data assimilation device is a blood pressure device 44, then the systolic and diastolic readings are displayed in alphanumeric form on the display screen 22. Similarly, if the selected data assimilation device is a thermometer 40, then an alphanumeric representation of temperature is displayed as it is being collected. If the selected device is the camera 28, then the recorded digital image is displayed on the display screen.

The health data tool 10 is optionally equipped with a speaker 56 associated with the housing 12. If the selected data assimilation device is a stethoscope 48, then the sound detected through the stethoscope microphone 54a is amplified and emitted through the speaker 56 to permit the health care provider to listen to the sound and readjust the position of the stethoscope as needed. Optionally, when the stethoscope 48 is selected, depressing input key 24c activates trigger 25 to cause the health data tool 10 to operate in record mode so that if a recording is desired, depressing the trigger 25 a first time begins the process of taking a digital sound recording and depressing the trigger 25 a second time ends the recording. Similarly, if the selected data assimilation device is a voice record, then depressing input key 24c activates microphone 54 to receive voice information and activates trigger 25 to function in record mode. Depressing the trigger 25 a first time begins the process of taking a digital voice recording and depressing the trigger 25 a second time ends the voice recording. In certain embodiments, the health data tool may also include a microprocessor programmed with voice recognition software to translate the sound recording into alphanumeric text.

When the data is a sound recording, ECG output, or other time-dependent data, such data is digitally recorded for a time period that in one embodiment, is selected by the health care provider. When such time dependent data assimilation devices are selected, input key 24E may be used to select the time period of the recording to store. In an alternative embodiment, the time period of the recording is the same as the time period that results from depressing the input trigger 25 on and off as described above. Alternatively, the health data tool 10 may be pre-preprogrammed to record and/or store particular types of health care data for a predetermined increment of time. For example, the health data tool 10 may be pre-programmed to record and store ECG data for a period of 60 seconds and to record and store stethoscope data for a period of 10 seconds.

The operation of the various input keys 24A-24E and trigger 25 described above is for exemplary purposes only. One of ordinary skill in the art will recognize that the input keys 24 can be programmed to perform the functions of the health data tool 10 in a variety of configurations. For example, even a single input key 24 can be configured with programming to select functions from a menu of options displayed on the display screen 22. Similarly, the functions of the trigger 25 can be accomplished using an input key 24. Accordingly, any arrangement of input keys 24 that allows the health care provider to operate the health data tool 10 to perform any of the functions described herein is suitable for the invention.

Furthermore, the embodiments of the health data tool 10 are described above as functioning in a sequential data assimilation mode, whereby one type of data assimilation device is activated at a time. In other advantageous embodiments, multiple data assimilation devices can be selected to simultaneously acquire different types of health care data, in which case the health data tool 10 functions as a multimeter, simultaneously acquiring and displaying a plurality of different data. In such embodiments, multiple devices are selected by sequentially depressing select input key 24*a* and enter key 24*b*. The display screen 22 initially displays each selected device in a list when entered. In one embodiment illustrated in FIG. 2, when acquire input key 24*c* is depressed, the display screen 22 is activated to display the different types of data on divided portions of the same display screen 22. Alternatively, multiple screens 22 are used to display different data on different types of screens. In such embodiments, simple alphanumeric data may be displayed on simple low resolution LED display screens, while more information intensive data such as wave form data or image data is displayed on a field emission, plasma, or other type of high resolution display screen.

In advantageous embodiments, the health data tool 10 is also equipped with an electronic memory 60 to store patient information and the health care data assimilated through the various data assimilation devices associated with the health data tool 10. As depicted in FIG. 1, the memory 60 is shown as a removable memory card, such as a flash memory card, that is inserted into memory slot 61. However, it is understood that the health data tool 10 may be configured with another type of memory such as conventional electronic memory 60 integrated within the housing 12. In an example operation, depressing store data input key 24*d* functions to store the health care data in the memory 60. Alternatively, the health data tool 10 may be programmed to automatically store the data in memory 60 when acquisition is complete. In an advantageous embodiment, the data is stored in a record structure associated with the patient identification information acquired using code reader 20. In certain embodiments, date and time information is automatically provided in the record, and time information is supplied from a clock (not shown) associated with the health data tool 10.

Figure 5:
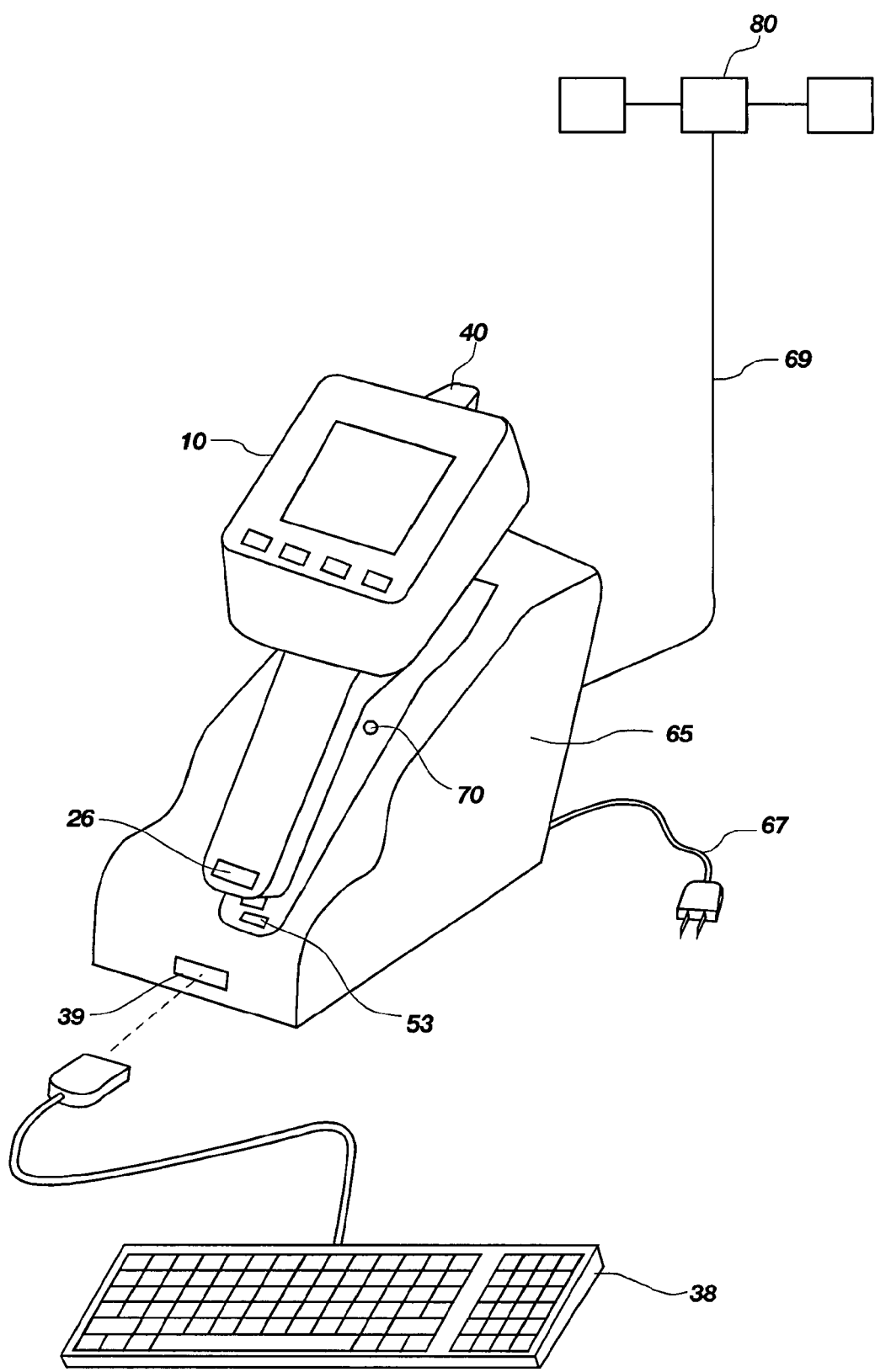
FIG. 5 is a front isometric view of an exemplary embodiment of a health data tool of the invention and a docking station for use therewith.
Figure 6A:
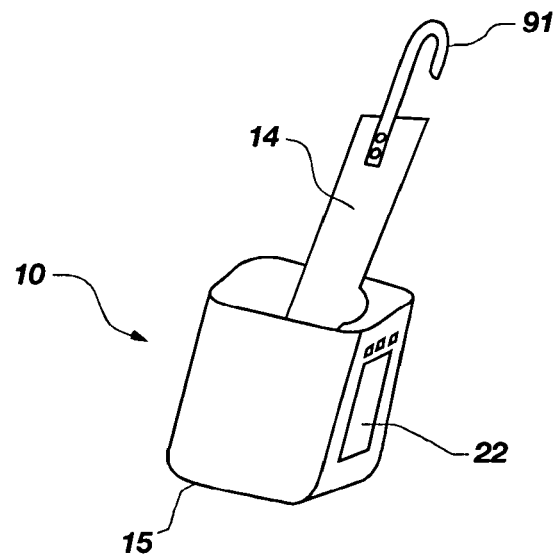
FIGS. 6A and 6B are isometric views of a belt attachment hook and a pole mount, respectively, associated with one embodiment of the health data tool of the invention.
Figure 6B:
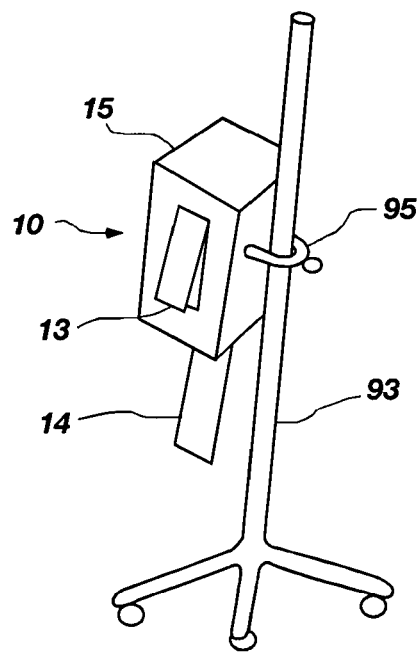

In further advantageous embodiments, the memory 60 stores a plurality of health care data records for a plurality of patients in a database structure. In such embodiments, the health care provider can acquire multiple records from multiple patients, or for the same patient, over the course of a shift and later upload the recorded information into a centralized database on a remote computer 80, as depicted in FIG. 5, that stores patient records as will be described more fully hereafter.

In certain advantageous embodiments, the health data tool 10 is also equipped with one or more data transmission devices 21 and/or data receiver devices 26. In one embodiment, the data transmitter 21 or receiver 26 device is a wireless data transmission device. Example wireless data transmission and receiver devices suitable for the invention include, but are not limited to, infrared and radio frequency transmitters and receivers. The data transmitter 21 is used to upload data stored in the memory 60 of the health data tool 10 into the remote computer system 80 via transmission of the data to remote infrared data or RF receiver. The data receiver 26 is used to receive an input of data into the health care tool 10 from a remote wireless data transmitter. Such remote transmitters and receivers are typically situated in individual rooms where the patient is located, in which case the data can be transmitted or received simultaneously in a given patient's room. Alternatively, these remote transmitters and receivers may be located in a central location where multiple data records for multiple patients may be uploaded or downloaded in a single session. Data transmission or reception is accomplished either automatically or by selecting a transmit or receive function from one of the input keys 24, which in certain embodiments, activates trigger 25 to function to initiate data transfer.

Another embodiment of a data transmission and receiver device is the computer input/output port 27. An appropriate data communication cable is attached to the input/output port 27 and to an input/output port for the central computer system. An advantage of using a standard computer interface cable is that is adaptable for use with any modifications, upgrades or other changes that are made to the health data tool 10 or the remote computer system 80.

Data transfer to the remote computer 80 may also be accomplished using docking port 51. The docking port 51 is specifically configured to plug the health data tool 10 into a data transfer port 53 situated in a docking station 65 as depicted in FIG. 5. The docking station 65 has a power supply cord 67 and outputs to a data transmission line 69 for transferring data between the remote computer system 80 and the data tool 10. In addition, the docking station 65 may include a battery recharging port 70 adapted to fit into recharging receptacle 71 in the health data tool 10 for recharging the batteries 13 housed therein. The docking station 65 may also include a keyboard data receiver port 39, which may be an infrared data port or cable type of port. Textual data may then be entered and stored into memory in the health data tool 10 via keyboard 38 that transmits the data either through the wireless receiver 21 associated with the health data tool 10 or through the data receiver port 39 associated with the docking station 65. In an exemplary practice, input key 24*e* is toggled to select a patient record stored into memory 60. Input select key 24*a* is toggled to select "text" data. The health data tool 10 is then activated to receive data entered from the keyboard 38, which is displayed in text format on screen 22 and ultimately transmitted to the remote computer system 80 with the other patient record data stored in the memory 60 of the health data tool 10.

The electronics required to operate the health data tool 10 are located within the housing 12. The electronics include a microprocessor that is programmed to perform the various functions described above for the health data tool 10. The operating electronics contains conventional busses, clocks, and logic necessary for communication between the microprocessor, the various data assimilation devices and the memory. The operating electronics also include the required circuitry for operating the display screen 22 responsively to the data output.

In certain embodiments, the data assimilation devices associated with the health data tool 10 contain separate microprocessors for converting the raw signal detected by transducers in the data assimilation devices into meaningful health care data. In these embodiments, only the converted health care data is input into the health data tool 10, thereby simplifying the electronics and lowering the cost of manufacturing the health data tool 10. These embodiments are adaptable for a wide variety of data assimilation devices now in existence or yet to be devised. In other embodiments, one or more microprocessors housed within the health data tool 10 are configured to perform the signal to data conversion functions of the data assimilation devices. In these embodiments, all or at least a portion of the electronics needed to perform the functions of the various data assimilation devices is also contained within the health data tool. Each of the example data assimilation devices described herein are well known to those of ordinary skill in the art, as is the circuitry required to perform the signal to data conversion functions of the devices.

The health data tool 10 of the invention is a versatile tool that is primarily meant to be used for portable applications, such as in taking patient data during rounds. However, the health data tool 10 may also be used for longer term monitoring. To facilitate both portability and long term usage, the health data tool may optionally be configured with a belt hook 91 and/or a pole mount 95 illustrated in FIG. 6. The belt hook 91 may be advantageously located in the handle 14 of the health data tool 10 and is used to conveniently attach the health data tool 10 to a belt worn by the health care provider. For long term monitoring, the pole mount 95 allows the health data tool to be securely mounted on a standard medical device pole 93 positioned by the patients bed.

Figure 7:
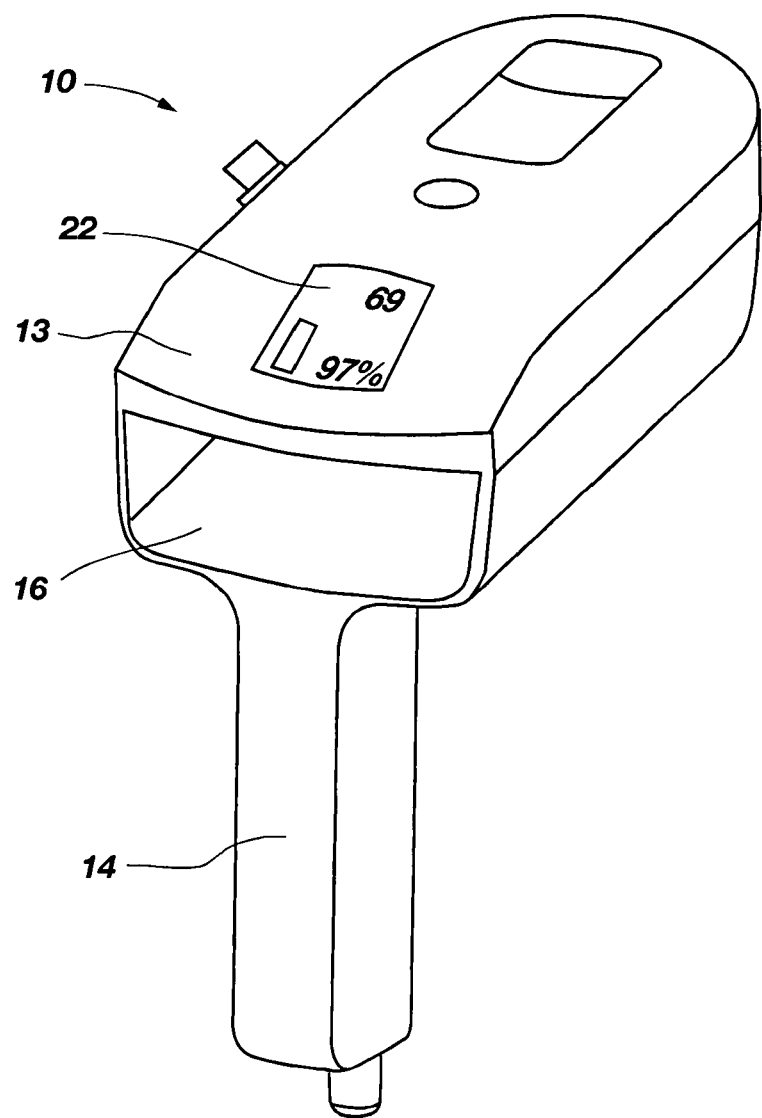
FIG. 7 is a front isometric view of another exemplary embodiment of a health data tool of the invention.
Figure 8:
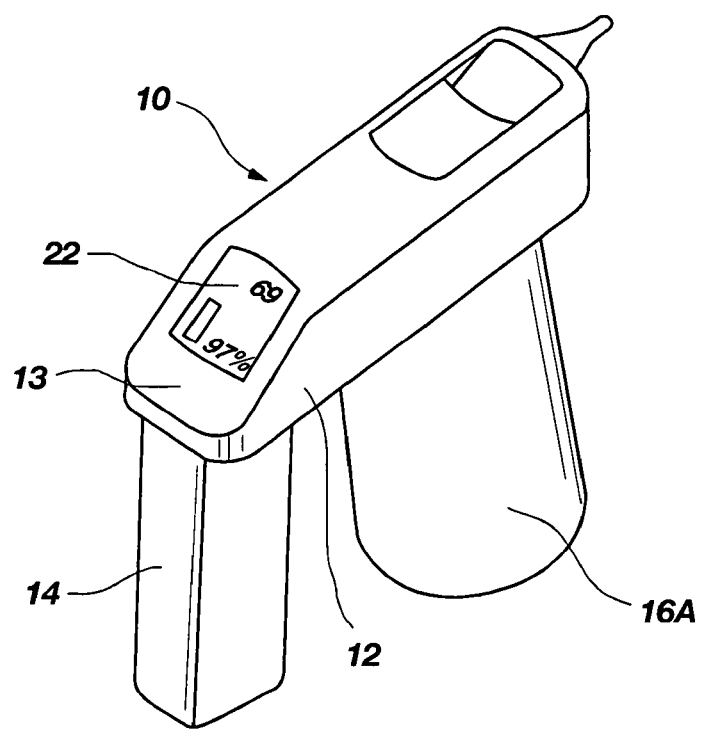
FIG. 8 is a front isometric view of another exemplary embodiment of a health data tool of the invention.
Figure 9:
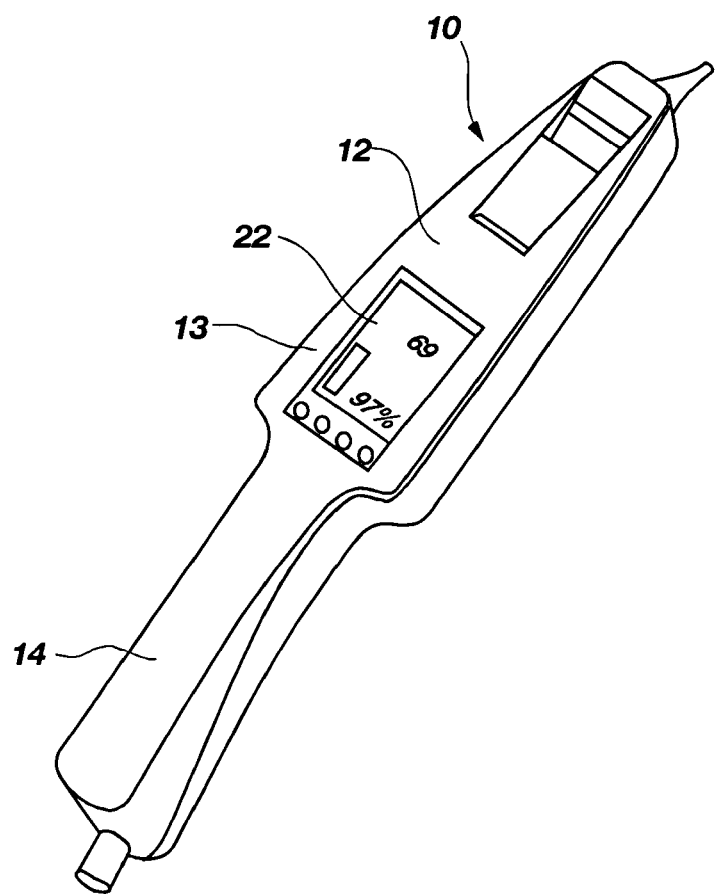
FIG. 9 is a front isometric view of another exemplary embodiment of a health data tool of the invention.
Figure 10:
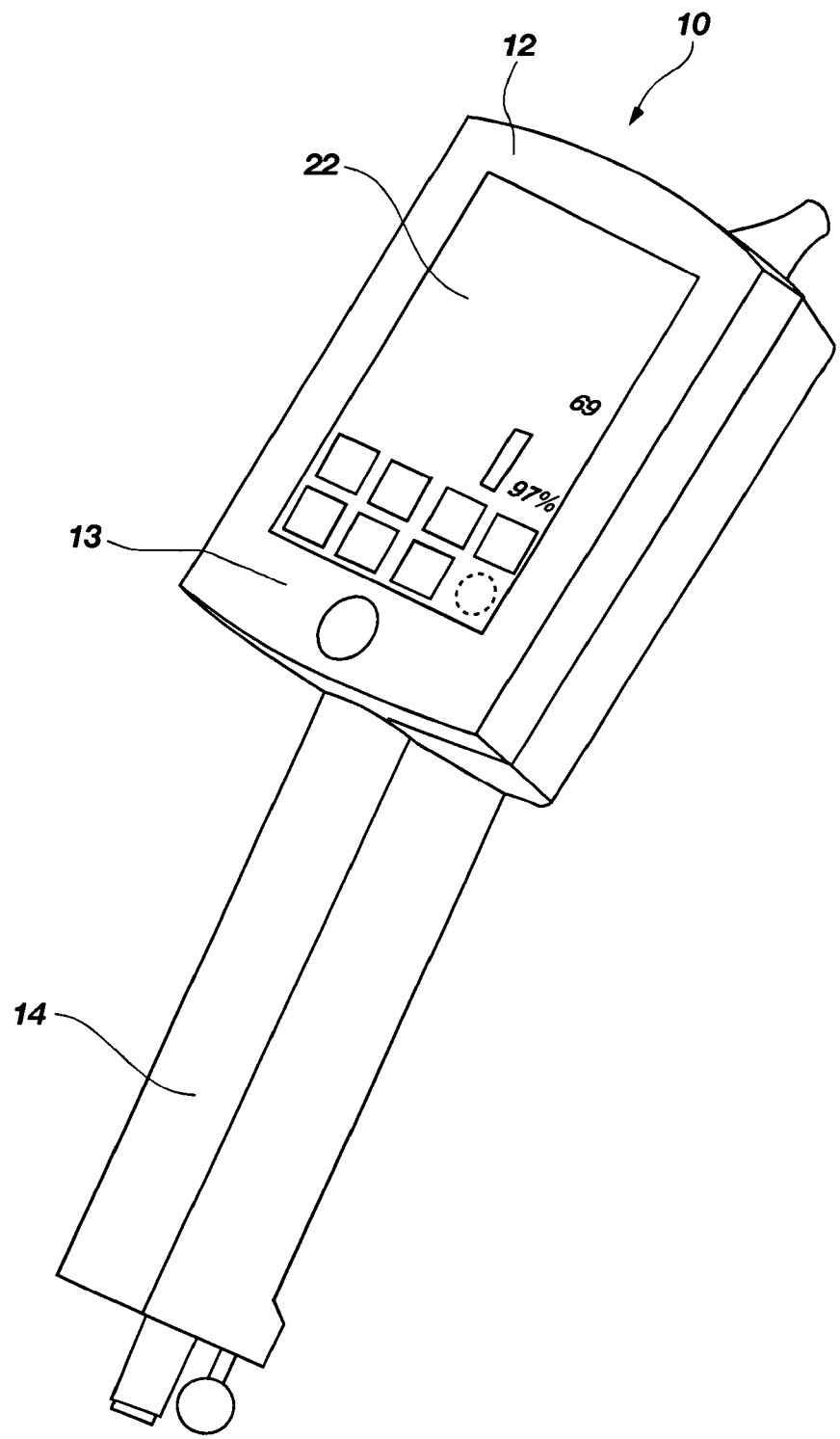
FIG. 10 is a front isometric view of another exemplary embodiment of a health data tool of the invention.

The overall structural configuration of the health data tool 10 can be implemented in numerous other forms as exemplified in FIGS. 7-10. FIG. 7 illustrates an "L" shaped configuration where the downwardly extending handle 14 is positioned at one end of the upper portion of the housing and perpendicular to the front surface 13 of the health data tool 10. The slot 16 for storing the blood pressure cuff 44 is positioned beneath the front surface 13 of the housing between the display 22 and the downwardly extending handle 14. FIG. 8 illustrates a variation on the "L" shaped configuration where a cylindrical blood pressure cuff compartment 16A is attached to a back surface opposite the front surface 13 of the housing 12. FIG. 9 and FIG. 3 illustrate "spearhead" configurations where the downwardly extending handle 14 has an upper surface that is continuous with the front surface 13 of the housing and upper surface of the housing containing the display 22 is flared at a medial position to define a junction between the handle 14 and the upper portion of the housing 12. FIG. 10 illustrates a "bent-T" shaped configuration where the downwardly extending handle 14 extends downwardly at an acute angle relative to the upper surface 13 of the health data tool 10.

From the foregoing it will be appreciated that, although specific embodiments of the invention have been described herein for purposes of illustration, various modifications may be made without deviating from the spirit and scope of the invention. Accordingly, the invention is not limited except as by the following claims.

What is claimed is:

1. A hand held health data tool defined by a housing having an upper and a lower portion, wherein a front surface of the upper portion supports a display screen and a plurality of input keys, and wherein the lower portion extends downwardly from one end of the upper portion at an angle relative to said front surface, the health data tool comprising:

a plurality of data assimilation devices, wherein more than one of said plurality of data assimilation devices simultaneously acquire a plurality of signal data related to a patient for simultaneous display on the display screen, and wherein at least one of said plurality of data assimilation devices is associated with the upper portion and at least another one of said plurality of data assimilation devices is associated with the lower portion;

a plurality of input ports associated with said plurality of data assimilation devices, wherein at least one of said plurality of input ports is a two-way input/output computer interface port, and wherein at least another one of said plurality of input ports is a plug-and-play switch port to automatically set the health data tool for acquiring signal data from a data assimilation device plugged into said plug-and-play switch port;

a code reader to associate the plurality of signal data with a plurality of patient information extracted from an identifying device associated with the patient;

a plurality of spaces configured to carry said plurality of data assimilation devices, wherein at least one of said plurality of spaces is associated with the upper portion and at least another one of said plurality of spaces is associated with the lower portion, wherein said plurality of spaces are configured as at least one of a hollow compartment or a receptacle, and wherein said plurality of data assimilation devices are securely held within said plurality of spaces using at least one of a door, a clamp, a hook, Velcro or a latch;

a microprocessor located within the housing for converting the plurality of signal data into health care data; and an electronic memory, located within the housing, to store said patient information and the health care data.

2. The health data tool of claim 1, wherein said angle is 90 degrees.

3. The health data tool of claim 1, wherein said angle is an acute angle.

4. The health data tool of claim 1, wherein said lower portion has an upper surface that is continuous with the front surface of the upper portion, and wherein said front surface is flared at a medial position to define a junction between the lower portion and the upper portion.

5. The health data tool of claim 1, wherein said plurality of data assimilation devices comprises at least two of a blood pressure sleeve, a thermometer, a pulse meter, an oximeter, a blood pressure measurement device, a stethoscope, a finger electrocardiogram unit, a lead wire electrocardiogram wire set, a digital camera, a microphone, or a hand pump configured for operating a blood pressure cuff.

6. The health data tool of claim 1, wherein said patient information comprises at least one of information pertaining to the patient's identity and information pertaining to at least one of a drug or device used by the patient.

7. The health data tool of claim 1, wherein said receptacle is configured for releasable insertion of a data assimilation device therein, and wherein the data assimilation device is secured within, and released from, said receptacle by closing and opening a latch mechanism.

8. The health data tool of claim 1, wherein the display screen displays any one or combination of wave form data, alpha numeric data or image data.

9. The health data tool of claim 1, wherein the health data tool is configured to occupy not more than 2 cubic feet of space and weigh not more than 10 pounds.

* * * * *